US010772997B2

(12) United States Patent
Shippert

(10) Patent No.: US 10,772,997 B2
(45) Date of Patent: Sep. 15, 2020

(54) TISSUE PARCELIZATION METHOD AND APPARATUS

(71) Applicant: Ronald D. Shippert, Littleton, CO (US)

(72) Inventor: Ronald D. Shippert, Littleton, CO (US)

(*) Notice: Subject to any disclaimer, the term of this patent is extended or adjusted under 35 U.S.C. 154(b) by 741 days.

(21) Appl. No.: 14/712,732

(22) Filed: May 14, 2015

(65) Prior Publication Data
US 2015/0374888 A1 Dec. 31, 2015

Related U.S. Application Data

(60) Provisional application No. 62/135,029, filed on Mar. 18, 2015, provisional application No. 61/993,834, filed on May 15, 2014.

(51) Int. Cl.
*A61M 1/00* (2006.01)
*A61B 17/00* (2006.01)

(52) U.S. Cl.
CPC .......... *A61M 1/0001* (2013.01); *A61M 1/008* (2013.01); *A61M 1/0023* (2013.01); *A61B 2017/00685* (2013.01); *A61B 2017/00969* (2013.01); *A61M 2202/08* (2013.01); *A61M 2205/75* (2013.01)

(58) Field of Classification Search
CPC .............. A61M 1/0001; A61M 1/0023; A61M 2202/08; A61M 2205/75; A61B 2017/00685; A61B 2017/00969
See application file for complete search history.

(56) References Cited

U.S. PATENT DOCUMENTS

| | | | |
|---|---|---|---|
| 1,138,764 | A | 5/1915 | Kline |
| 3,223,490 | A | 12/1965 | Sacken et al. |
| 3,434,869 | A | 3/1969 | Davidson |
| 3,664,387 | A | 5/1972 | Cates, Jr. |
| 3,693,673 | A | 9/1972 | Oates |
| 3,993,080 | A | 11/1976 | Loseff |
| 4,346,711 | A | 8/1982 | Agdanowski et al. |

(Continued)

FOREIGN PATENT DOCUMENTS

| | | |
|---|---|---|
| EP | 1531881 | 5/2005 |
| EP | 1531882 | 5/2005 |

(Continued)

OTHER PUBLICATIONS

U.S. Appl. No. 13/174,169, filed Jun. 30, 2011, Shippert.
(Continued)

*Primary Examiner* — Tatyana Zalukaeva
*Assistant Examiner* — Gabriella E Burnette
(74) *Attorney, Agent, or Firm* — Sheridan Ross P.C.

(57) ABSTRACT

Methods and systems for sizing fat parcels are provided. In particular, a parcelizer device that includes a container and a displacement insert or filter element is provided. Tissue containing fat parcels is passed through the parcelizer. The parcelizer can include multiple displacement inserts or filter elements. Alternatively or in addition, a plurality of displacement structures that each include one or more displacement inserts or filter elements can be provided. In general, the displacement inserts or filter elements are configured to progressively reduce the size of fat parcels included in tissue.

16 Claims, 12 Drawing Sheets

(56) References Cited

U.S. PATENT DOCUMENTS

| | | |
|---|---|---|
| 4,359,049 A | 11/1982 | Redl et al. |
| 4,447,230 A | 5/1984 | Gula et al. |
| 4,492,258 A | 1/1985 | Lichtenstein et al. |
| 4,548,207 A | 10/1985 | Reimels |
| 4,683,884 A | 8/1987 | Hatfield et al. |
| 4,753,634 A | 6/1988 | Johnson |
| 4,770,187 A | 9/1988 | Lash et al. |
| D298,650 S | 11/1988 | Lash |
| 4,834,703 A | 5/1989 | Dubrul et al. |
| 4,883,755 A | 11/1989 | Carabasi et al. |
| 4,957,492 A | 9/1990 | McVay |
| 5,002,538 A | 3/1991 | Johnson |
| 5,035,708 A | 7/1991 | Alchas et al. |
| 5,049,146 A | 9/1991 | Bringham et al. |
| 5,052,999 A | 10/1991 | Klein |
| 5,158,533 A | 10/1992 | Strauss et al. |
| 5,312,380 A | 5/1994 | Alchas et al. |
| 5,338,294 A | 8/1994 | Blake, III |
| 5,352,194 A | 10/1994 | Greco et al. |
| 5,352,410 A | 10/1994 | Hansen et al. |
| 5,372,945 A | 12/1994 | Alchas et al. |
| 5,441,539 A | 8/1995 | Alchas et al. |
| 5,569,178 A | 10/1996 | Henley |
| 5,603,845 A | 2/1997 | Holm |
| 5,766,134 A | 6/1998 | Lisak et al. |
| 5,786,207 A | 7/1998 | Katz et al. |
| 5,804,366 A | 9/1998 | Hu et al. |
| 5,827,217 A | 10/1998 | Silver et al. |
| 5,911,700 A | 6/1999 | Mozsary et al. |
| 5,976,470 A | 11/1999 | Maiefski et al. |
| 6,013,048 A | 1/2000 | Podany et al. |
| 6,024,725 A | 2/2000 | Bollinger et al. |
| 6,258,054 B1 | 7/2001 | Mozsary et al. |
| 6,299,763 B1 | 10/2001 | Ashman |
| 6,303,286 B1 | 10/2001 | Dennis et al. |
| 6,315,756 B1 | 11/2001 | Tankovich |
| 6,316,247 B1 | 11/2001 | Katz et al. |
| 6,468,225 B1 | 10/2002 | Lundgren |
| 6,494,876 B1 | 12/2002 | Fowler et al. |
| 6,623,733 B1 | 9/2003 | Hossainy et al. |
| 6,626,890 B2 | 9/2003 | Nguyen et al. |
| 6,777,234 B1 | 8/2004 | Dennis et al. |
| 6,905,660 B2 | 6/2005 | Harper et al. |
| 6,991,765 B2 | 1/2006 | Neilson et al. |
| 7,097,690 B2 | 8/2006 | Usher et al. |
| 7,121,309 B2 | 10/2006 | Goemans et al. |
| 7,335,513 B2 | 2/2008 | Smith et al. |
| 7,390,484 B2 | 6/2008 | Fraser et al. |
| 7,687,059 B2 | 3/2010 | Fraser et al. |
| 7,767,098 B2 | 8/2010 | Vida |
| 7,771,754 B2 | 8/2010 | Memar |
| 7,780,649 B2 | 8/2010 | Shippert |
| 7,789,872 B2 | 9/2010 | Shippert |
| 7,794,449 B2 | 9/2010 | Shippert |
| 8,062,286 B2 | 11/2010 | Shippert |
| 8,100,874 B1 | 1/2012 | Jordan et al. |
| 8,333,740 B2 | 12/2012 | Shippert |
| 8,579,852 B2 | 11/2013 | Memar et al. |
| 8,622,997 B2 | 1/2014 | Shippert |
| 8,887,770 B1 | 11/2014 | Shippert |
| 9,044,547 B2 * | 6/2015 | Tremolada ............ C12M 45/02 |
| 9,867,788 B2 * | 1/2018 | Schroeder ............. A61K 31/00 |
| 2002/0146817 A1 | 10/2002 | Cannon et al. |
| 2002/0198474 A1 | 12/2002 | Becker |
| 2003/0161816 A1 | 8/2003 | Fraser et al. |
| 2003/0162707 A1 | 8/2003 | Fraser et al. |
| 2004/0067219 A1 | 4/2004 | Vida |
| 2004/0097867 A1 | 5/2004 | Fraser et al. |
| 2005/0025755 A1 | 2/2005 | Hedrick |
| 2005/0084961 A1 | 4/2005 | Hedrick et al. |
| 2005/0186671 A1 | 8/2005 | Cannon et al. |
| 2006/0093527 A1 | 5/2006 | Buss |
| 2006/0258004 A1 | 11/2006 | Kosnik et al. |
| 2008/0014181 A1 | 1/2008 | Ariff et al. |
| 2008/0058763 A1 | 3/2008 | Boland et al. |
| 2009/0192454 A1 | 7/2009 | Boland et al. |
| 2014/0130936 A1 | 5/2014 | Shippert |
| 2014/0202959 A1 * | 7/2014 | Rothman ................. B03B 1/04 |
| | | 210/660 |
| 2017/0000518 A1 * | 1/2017 | Smith ............ A61B 17/320758 |
| 2017/0002323 A1 * | 1/2017 | Tremolada ............ C12M 45/02 |

FOREIGN PATENT DOCUMENTS

| | | |
|---|---|---|
| EP | 1921133 | 5/2008 |
| WO | WO 2000/77164 | 12/2000 |
| WO | WO 2004/067065 | 8/2004 |
| WO | WO 2005/011569 | 2/2005 |
| WO | WO 2005/012480 | 2/2005 |
| WO | WO 2005/034843 | 4/2005 |
| WO | WO 2005/095581 | 10/2005 |
| WO | WO 2006/014156 | 2/2006 |
| WO | WO 2006/014159 | 2/2006 |
| WO | WO 2006/022612 | 3/2006 |
| WO | WO 2006/026969 | 3/2006 |
| WO | WO 2006/127007 | 11/2006 |
| WO | WO 2008/137234 | 11/2008 |
| WO | WO 2009/149691 | 12/2009 |

OTHER PUBLICATIONS

Genesis Biosystems, Advancing the Science of Skincare, LipiVage, 1 page, at http://www.dermagenesis.com/prodlipivage.cfm, printed Oct. 25, 2004.

Genesis Biosystems, Advancing the Science of Skincare, LipiVage, 3 pages, at http://www.dermagenesis.com/prodlipivage.cfm, printed Mar. 16, 2005.

LipiVage Fat Harvest, Wash & Transfer System, available at www.lipivage.com, Genesis Biosystems, Inc., 2 pages, printed Sep. 21, 2005.

LipiVage, product insert, 2 pages, Aug. 2004.

"Innovative Time-Saving Products, vol. VII," Shippert Medical Technologies Incorporated, Apr. 2010, 40 pages.

* cited by examiner

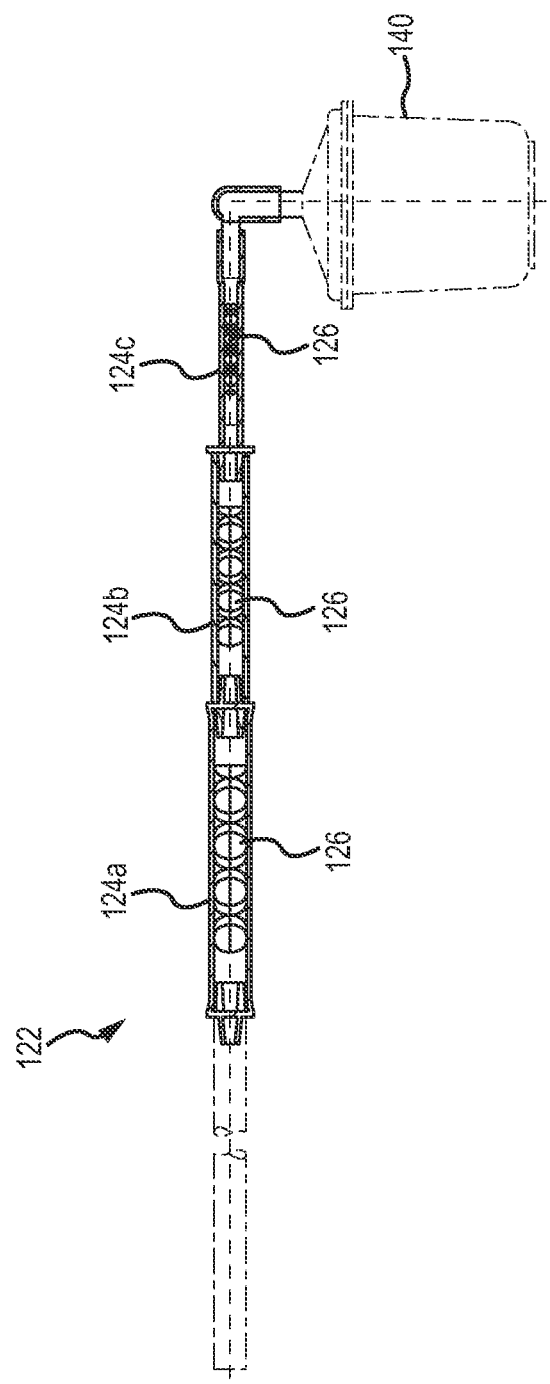

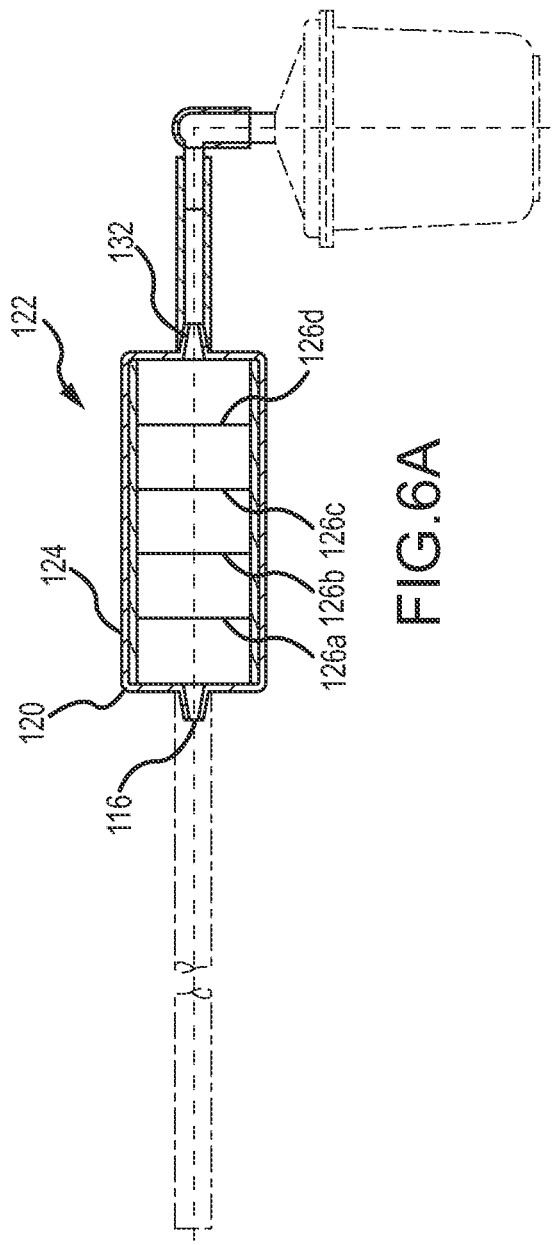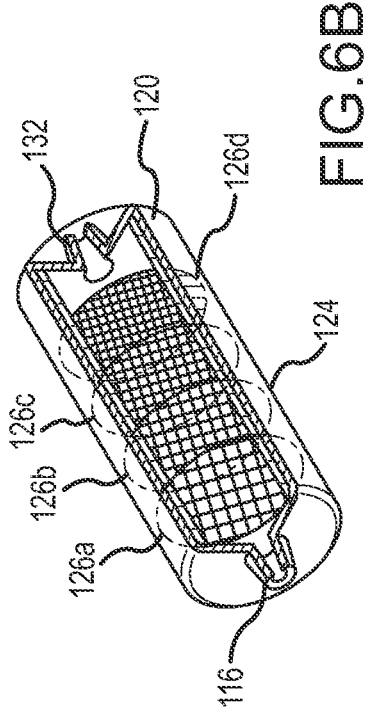

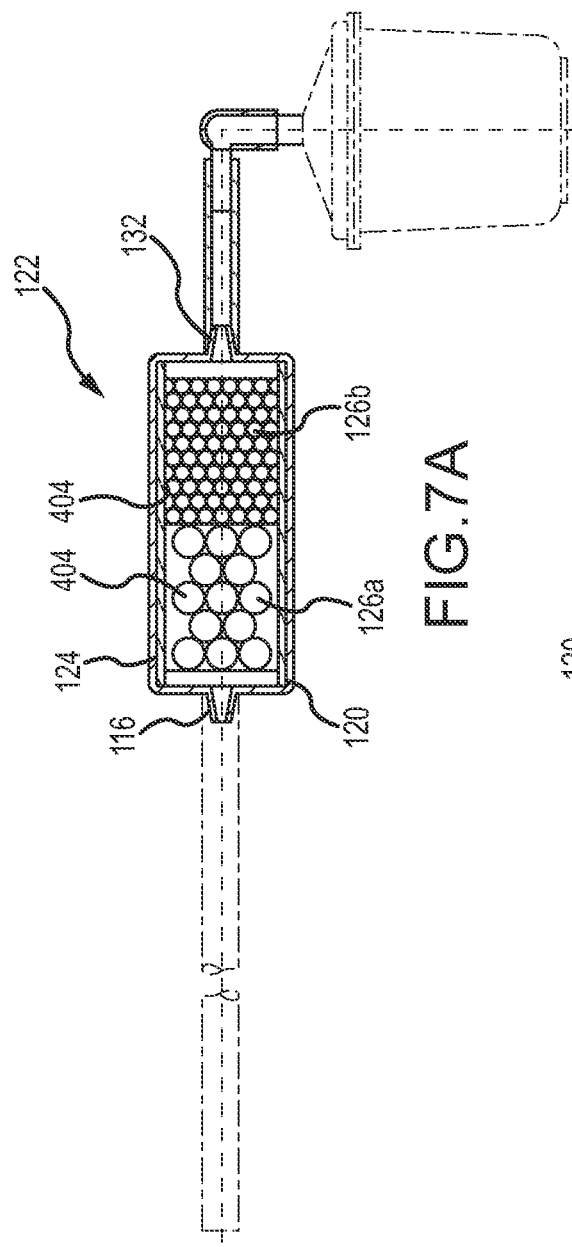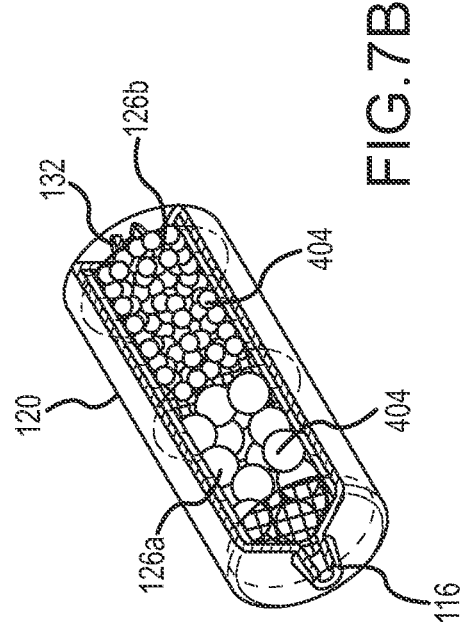

TISSUE PARCELIZATION METHOD AND APPARATUS

CROSS-REFERENCE TO RELATED APPLICATIONS

This application claims the benefit of U.S. Provisional Patent Application Ser. No. 61/993,834, filed May 15, 2014, and U.S. Provisional Patent Application Ser. No. 62/135,029, filed Mar. 18, 2015, the entire disclosures of which are hereby incorporated herein by reference.

FIELD

The present disclosure provides tissue parcelization methods and apparatuses that achieve a desired fat parcel size, while maintaining acceptable harvest times.

BACKGROUND

Fat parcelization is the reduction in size of the fat bolus that is produced during fat harvest with a cannula. Several factors control the fat parcel sizing during the harvest of the fat. The greatest influence on the size of the fat parcel is the hole diameter of the cannula. Other factors include the vacuum power used to suck the fat through the hole, and the length of the surgeon's "stroke" during harvest.

Parcelization is needed when transplanting fat during autologous fat transfer/grafting. Presently, the cannulas that are used to parcelize the harvested fat are typically 3 and 4 mm outside diameter cannulas with various hole patterns. These commonly used cannulas will produce fat parcels that are less than 10 mm in diameter. This is because the fat parcels are very compressible and flexible, and relatively large parcels can squeeze through small channels. However, these relatively large fat parcels can plug reinjection needles and equipment. In addition, 10 mm fat parcels are now thought to be too large to ensure that the fat parcel survives reinjection. In particular, it is believed that parcels of this size are too large for nutrients to pass to the interior of the parcel. Recent studies indicate that fat parcels with a diameter of less than 3 mm (for example, about 1 mm) are preferred. In particular, this size should be favorable for ensuring growth in the new location, while avoiding clogging of the tissue transfer hardware.

The size of the fat parcels can be decreased by decreasing the size of the holes in the harvest cannula. However, this slows the harvest procedure unacceptably. Other techniques reduce the size of fat parcels by pulverizing them. However, this can destroy the fat parcels, with the result that they will not revascularize when placed in their new location.

SUMMARY

Embodiments of the present disclosure provide a parcelizer device that presents a convoluted, circuitous or otherwise non-linear path to harvested tissue. Alternatively or in addition, the parcelizer device includes a series of elements that present a non-linear path to harvested tissue, elements that size fat parcels, or both. This reduces the size of fat parcels included in the harvested tissue. In particular, a relatively gentle process in which the fat parcels are resized as the parcels are moved over or around obstacles in the non-linear path is provided. The size of the fat parcels can be controlled through an appropriate passage size within the non-linear path. Moreover, at least some embodiments of the present disclosure do not make the size of the parcels smaller than the smallest dimension presented by the non-linear path or the sizing elements.

In accordance with embodiments of the present disclosure, a parcelizer device or a system for sizing fat parcels is provided. The system can include a cannula, and a container that defines a first volume. The container includes an inlet that is connected to an outlet of the cannula, and an outlet. A displacement structure is held within the first volume of the container. The displacement structure defines at least a first non-linear path between the inlet and the outlet of the container. The system can additionally include a tissue reservoir with an inlet that is interconnected to the outlet of the container. In accordance with further embodiments, the system can include a power source in the form of a vacuum source that draws tissue through at least the cannula and the first volume of the container. In accordance with still other embodiments, the system can include a power source in the form of a pressure source that pushes tissue through a displacement structure.

In accordance with further embodiments of the present disclosure, the displacement structure defines at least a first non-linear pathway within the first volume. For example, the displacement structure can be in the form of a screw or auger that is fixed within a container. A particle is then caused to move around and along a first axis of the container, corresponding to a center axis of the auger. As the particle moves along the axis, the particle is displaced by the blades of the auger, thus causing the particle to also moves around the axis in a clockwise or counter-clockwise direction. The pathway defined by the fixed auger can revolve in a first direction with respect to a first axis of the container for a first segment along the first axis, and in a second direction respect to the first axis of the container for a second segment along the first axis. Accordingly, a particle can be moved in a first one of a clockwise or counter clockwise direction by the first segment and in a second one of the clockwise or counter-clockwise direction by the second segment as it is drawn along the length of the auger. Moreover, the displacement structure may comprise an insert with a central shaft aligned with the first axis of the container and a helical surface surrounding the central shaft.

In accordance with other embodiments of the present disclosure, the displacement structure can include a plurality of elements that define multiple non-linear paths between the inlet and the outlet of the container. As examples, the plurality of elements can include a plurality of beads. The beads can be spherical, hemispherical, faceted, or any other shape. In accordance with still further embodiments, the beads can include one or more through-holes. Alternatively, or in addition, the beads may be solid having no holes. For example, a bead with no holes may be spherical, hemispherical, faceted, or any other shape. Similarly, the plurality of elements may include a combination of beads having different shapes, sizes, and/or holes. As yet another example, the plurality of elements can include tubes. The plurality of elements can be held loosely within the first volume of the container, and/or can be held in a defined pattern.

In accordance with still other embodiments of the present disclosure, the displacement structure can include one or more filter or sizing elements. A filter or sizing element may comprise a mesh, screen, mat, perforated plate, perforated plate with raised edges, or other material or structure that provides holes of a selected size or range of sizes.

A parcelizer device or system for sizing fat parcels, also referred to herein as simply a "parcelizer", can include multiple displacement structures. For example, a series of displacement structures that progressively reduce the size of fat parcels can be provided. The displacement structures can be all of the same type, or can include any combination of different displacement structures. In accordance with still other embodiments, different displacement structures can be located within a single container.

Additional features and embodiments of the present disclosure will become more readily apparent from the following description, particularly when considered in connection with the accompanying drawings.

BRIEF DESCRIPTION OF THE DRAWINGS

FIG. 5 depicts displacement structures in accordance with embodiments of the present disclosure;

FIG. 6A depicts displacement structures in accordance with other embodiments of the present disclosure in a cross-section taken in elevation;

FIG. 6B is a cut away, perspective view of the displacement structures of FIG. 6A;

FIG. 7A depicts displacement structures in accordance with other embodiments of the present disclosure in a cross-section taken in elevation;

FIG. 7B is a cut-away view of the displacement structures of FIG. 7A;

DETAILED DESCRIPTION

Figure 1A:
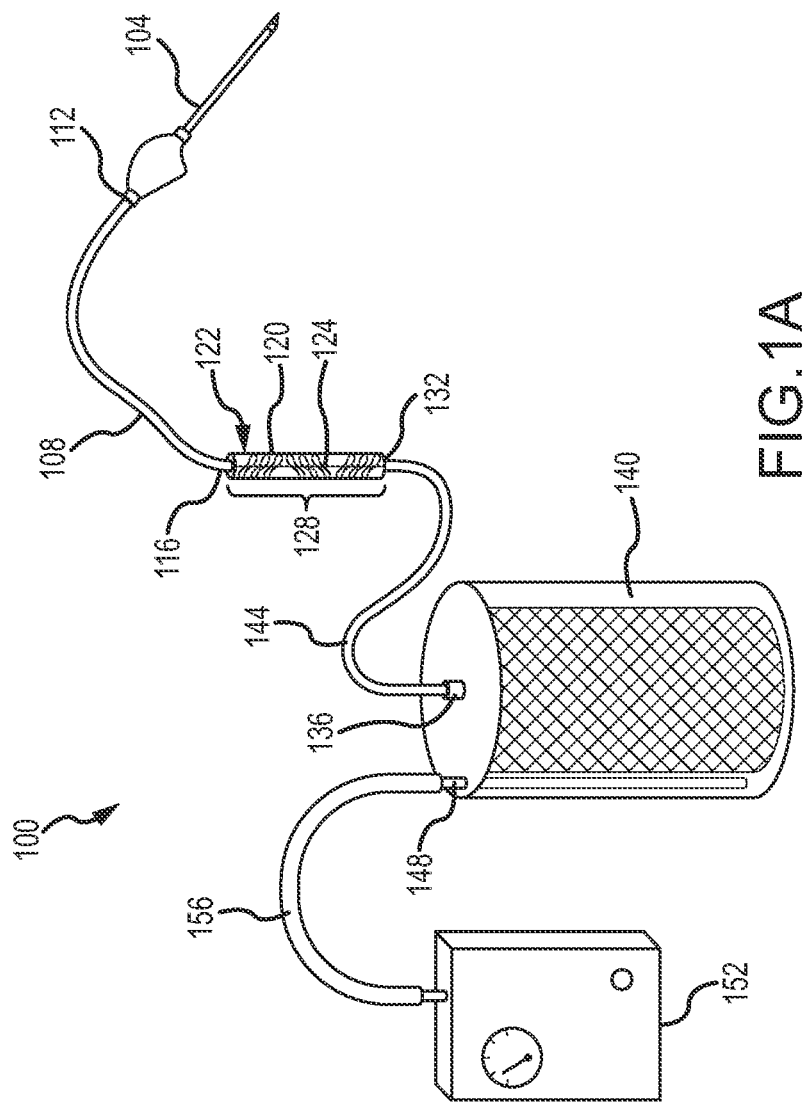
FIG. 1A depicts a tissue parcelization system in accordance with embodiments of the present disclosure.

FIG. 1A depicts a tissue parcelization system 100 in accordance with embodiments of the present disclosure. In general, the system 100 includes a cannula 104, and a length of tubing 108 connecting an outlet 112 of the cannula 104 to the inlet 116 of a container 120. A parcelizer device 122 is formed from a displacement structure 124 located within a first volume 128 defined by the container 120. As described in greater detail elsewhere herein, the displacement structure 124, in cooperation with the walls of the container 120 forming the first volume 128, defines a convoluted, circuitous, or otherwise non-linear path through which tissue drawn in through the inlet 116 of the container and out an outlet 132 of the container 120 must pass. Alternatively or in addition, the displacement structure can define pathways of decreasing cross-sectional area. The outlet 132 of the container 120 can be connected to an inlet 136 of a reservoir 140 by a reservoir conduit 144. An outlet 148 of the reservoir 140 can then be connected to a vacuum source 152 by a length of vacuum conduit 156. As can be appreciated by one of skill in the art, by applying a vacuum, adipose tissue can be drawn in through the cannula 104 from a collection site, through the parcelizer device 122 where the fat parcels are reduced in size, and deposited in the reservoir 140.

Figure 1B:
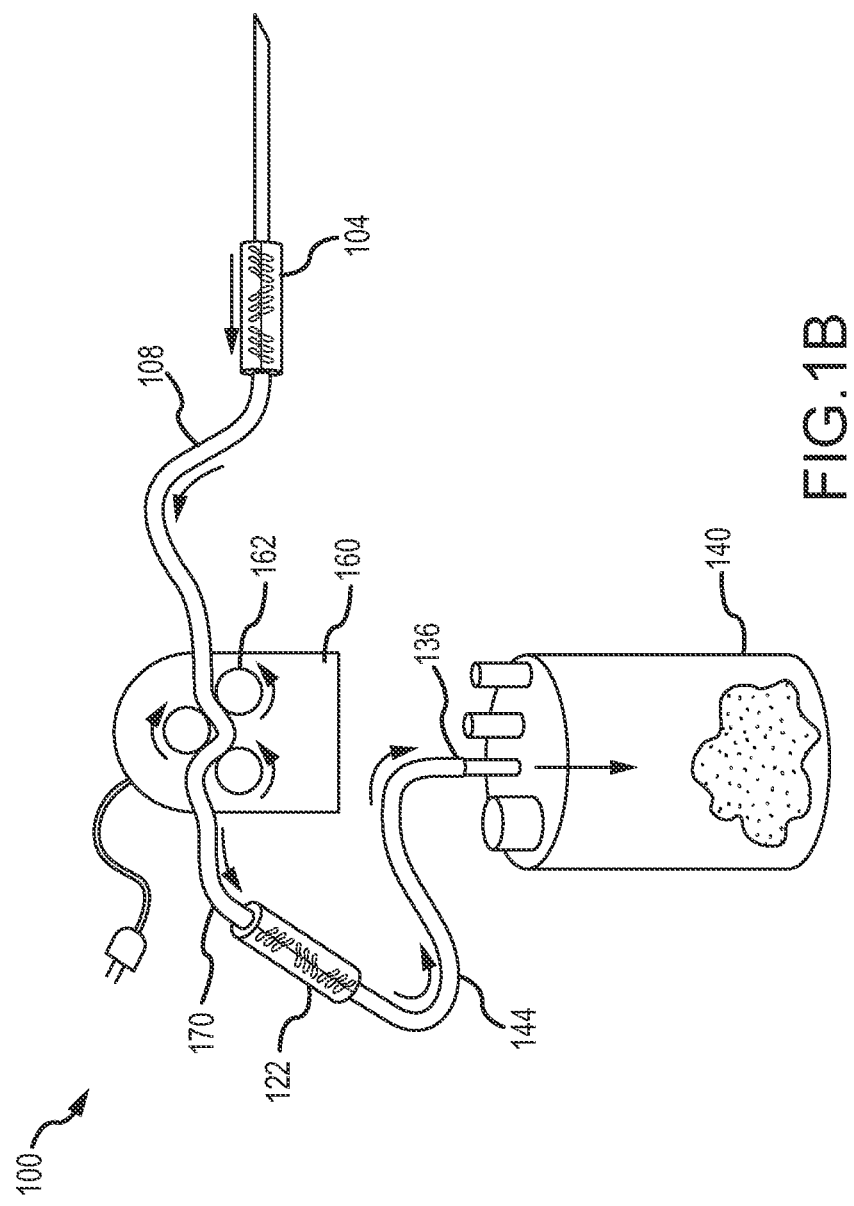
FIG. 1B depicts a tissue parcelization system in accordance with other embodiments of the present disclosure.

FIG. 1B depicts a tissue parcelization system 100 in accordance with other embodiments of the present disclosure. In particular, the system 100 in FIG. 1B utilizes a pressure source 160, such as a peristaltic pump, instead of the vacuum source 152 discussed in relation to FIG. 1A. In such an embodiment, a length of tubing 108 connects an outlet of the cannula 104 to the pressure source 160 and a length of tubing 170 connects the pressure source 160 to the parcelizer device 122. The parcelizer device 122 can be identical to the parcelizer device 122 as used in connection with the embodiment discussed in relation to FIG. 1A. Accordingly, the parcelizer device 122 can include a displacement structure 124 located within a first volume 128 defined by a container 120. However, instead of being pulled through the parcelizer device 122, the adipose tissue is pushed through the parcelizer device 122 by the pressure created by the pressure source 160. That is, a vacuum created by a peristaltic pump draws adipose tissue in through the cannula 104 from a collection site. The adipose tissue is then pushed through the parcelizer device 122 by the pressure created by the pressure source 160, where fat parcels are reduced in size and deposited in the reservoir 140. Although the pressure source 160 is illustrated as having tubing or conduit passing through three rollers 162, other configurations are contemplated. For example, the pressure source 160 may include other types of peristaltic pumps having a rotor with a number of rollers or lobes that are attached to an external circumference of the rotor such that as the rotor compresses a flexible tube, the adipose tissue is forced, or pumped, through the tube. Similarly, other types of positive displacement pumps may be utilized.

Figure 1C:
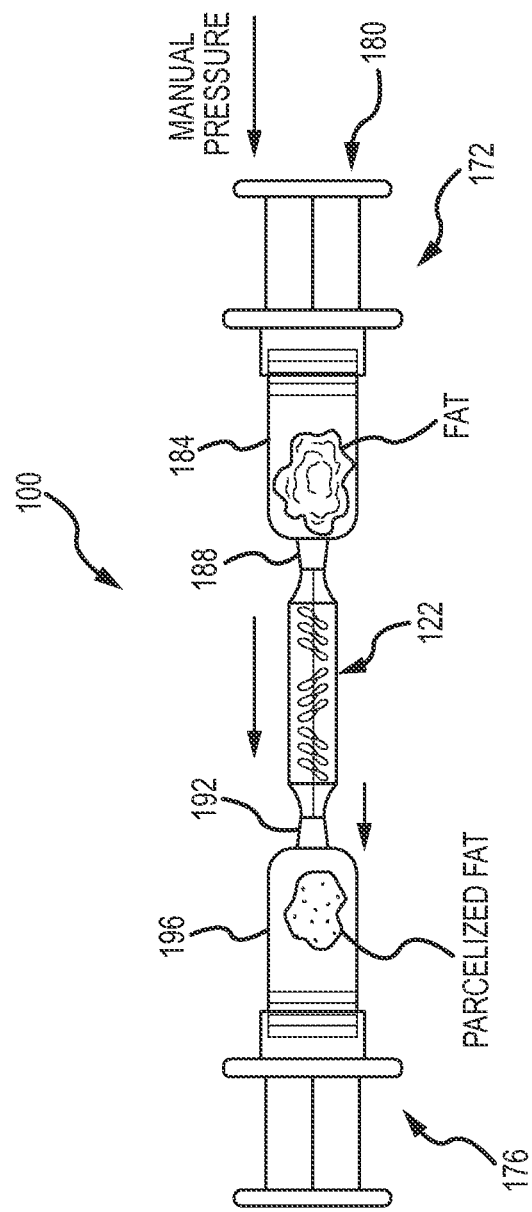
FIG. 1C depicts a tissue parcelization system in accordance with other embodiments of the present disclosure.

FIG. 1C depicts a tissue parcelization system 100 in accordance with other embodiments of the present disclosure. In particular, the system 100 in FIG. 1C utilizes pressure created by the application of manual pressure to a syringe, such as syringe 172. In such an embodiment, a barrel 184 of the syringe 172 may contain adipose tissue; the syringe tip 188, also referred to as an adapter, is connected to an inlet of the parcelizer device 122. An outlet of the parcelizer device 122 is connected to a tip of another syringe 176. The parcelizer device 122 can be identical to the parcelizer device 122 as used in connection with the embodiment discussed in relation to FIG. 1A. Accordingly, the parcelizer device 122 can include a displacement structure 124 located within a first volume 128 defined by a container 120. Therefore, as manual pressure is applied to a plunger 180 of the syringe 172, the previously collected adipose tissue residing in barrel 184 is pushed through the parcelizer device 122. Accordingly, the adipose tissue is then pushed through the parcelizer device 122, where fat parcels are reduced in size and deposited into the barrel 196 of syringe 176. In accordance with embodiments of the present disclosure, the tip 188 of syringe 172 may be directly connected to the parcelizer device 122, or the tip 188 of syringe 172 may be connected to the parcelizer device 122 using a length of tubing or conduit. Similarly, the tip 192 of syringe 176 may be directly connected to the parcelizer device 122, or the tip 192 of syringe 176 may be connected to the parcelizer device 122 using a length of tubing or conduit. Alternatively or in addition, the resized fat parcels can be reinjected into a body through a syringe 176.

Figure 2A:
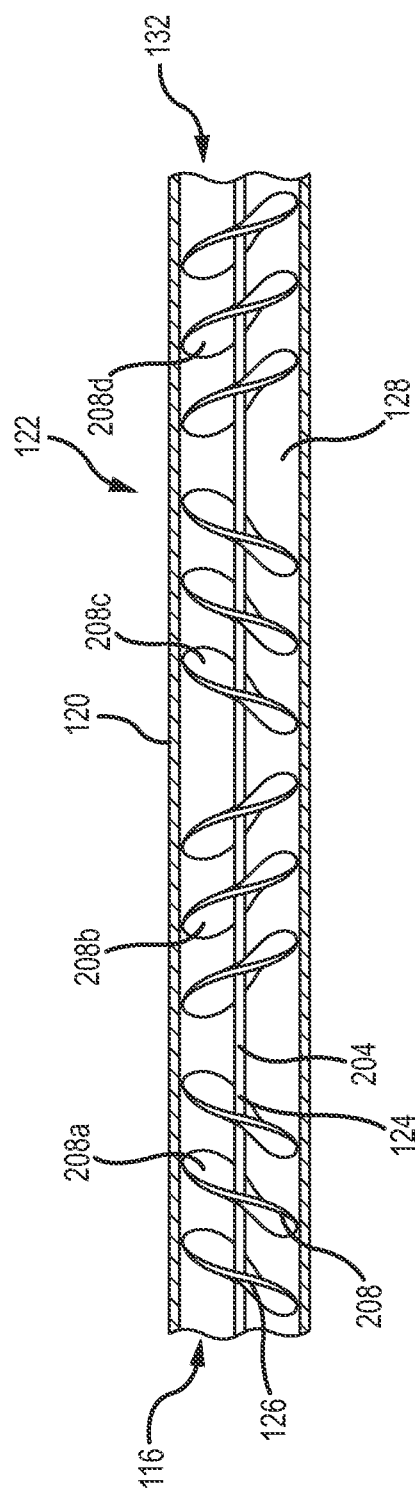
FIG. 2A-2D depict containers and displacement structures of tissue parcelization systems in accordance with various embodiments of the present disclosure.

FIG. 2A depicts a container 120 that is provided as part of a displacement structure 124 of a parcelizer device 122 in accordance with an embodiment of the present disclosure. In this example, the container 120 is cylindrical. The displacement structure 124 includes a displacement insert 126 having an outside diameter that is about the same as, smaller than, or slightly larger than the interior diameter of the container 120. Moreover, the displacement insert 126 includes a central shaft 204 that is generally aligned with a longitudinal axis of the container 120. The central shaft 204 is surrounded by a helical surface 208. The helical surface 208 includes first and third helical surfaces 208*a* and 208*c* that revolve in a first direction with respect to the length of the central shaft 204, and second and fourth helical surfaces 208*b* and 208*d* that revolve in a second direction with respect to the central shaft 204. A space may be provided between the edge of the helical surfaces 208 and the inside surface of the container 120. As can be appreciated by one of skill in the art after consideration of the present disclosure, the displacement insert 126 is fixed relative to the container 120, and the term "revolve" refers to the effect of the displacement insert 126 on a fat parcel passing through the parcelizer device 122 in this embodiment. In particular, the blades of the insert 126 causes the fat parcel to travel around a central axis of the insert 126 as the fat parcel is moved along the length of the parcelizer device 122. Although first, second, third and fourth helical surfaces 208*a*-208*d* are shown in this example, embodiments of such a displacement insert 126 can include one or more helical surfaces 208. In accordance with embodiments of the present disclosure, the displacement insert 126 may therefore comprise a screw or Archimedes screw that periodically reverses direction, and that remains fixed relative to the container 120. As an example, but without limitation, the container 120 in this embodiment may comprise a length of flexible tubing, including but not limited to a length of tubing interconnected to the outlet 112 of the cannula 104. In such an embodiment, the inlet 116 and the outlet 132 may simply be the sections of the tubing at the ends of the displacement structure 124, with the first volume 128 comprising the volume or section of tubing in which the displacement insert 126 is placed. Alternatively, the container 120 in such an embodiment may comprise a rigid cylinder.

Figure 2D:
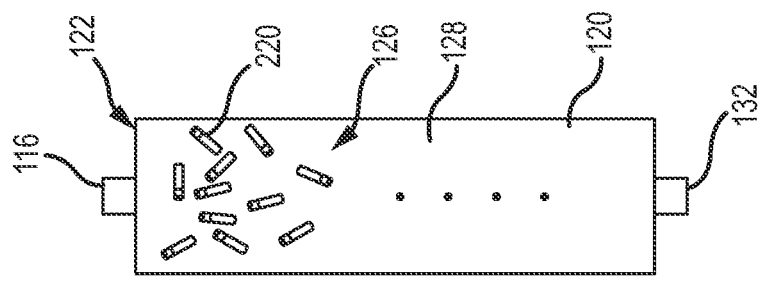
Figure 2C:
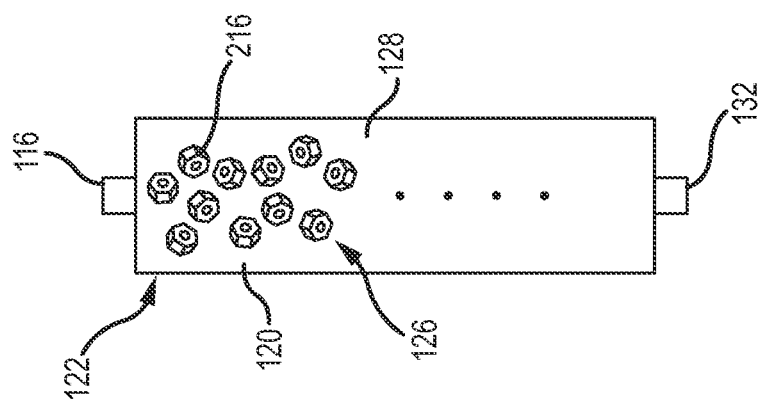
Figure 2B:
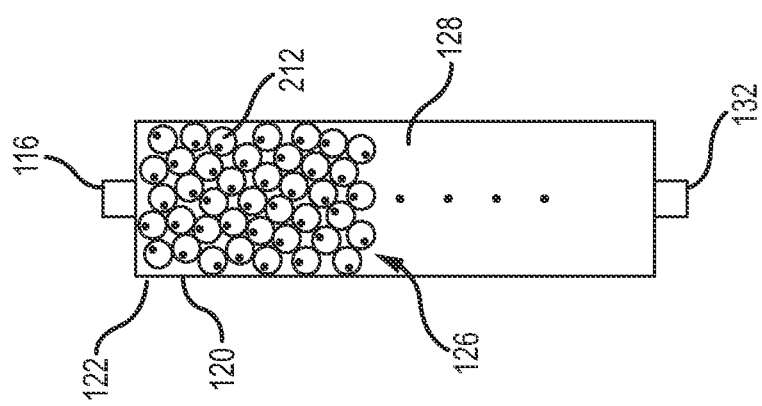

FIG. 2B depicts a container 120 and a displacement insert 126 of a displacement structure 124 included in a parcelizer device 122 in accordance with a further embodiment of the present disclosure. In this embodiment, the displacement structure 124 includes a displacement insert 126 that is in the form of a plurality of elements 212 that define multiple non-linear paths between the inlet 116 and the outlet 132 of the container 120. In this example, the plurality of elements 212 comprise spherical beads with a through-hole and/or spherical beads, or balls, without a through-hole. In an alternate configuration, such as depicted in FIG. 2C, a displacement structure 124 can include a plurality of elements 216 that comprise faceted beads with a through-hole. In accordance with still other embodiments, such as is depicted in FIG. 2D, a displacement structure 124 can include a plurality of elements 220 that comprise tubes or straws. In the embodiments shown in FIGS. 2B-2C, the elements of 212, 216, 220 of the displacement insert 126 are poured or otherwise introduced into the first volume 128 of the container 120, such that the individual elements 212, 216, 220 are randomly oriented within that volume 128. In accordance with other embodiments, the displacement insert 126 can include elements that are oriented in a predefined manner. Although the first volume 128 defined by the container 120 in each of the embodiments depicted in FIGS. 2B-2D is shown only partially filled, it can be appreciated by one of skill in the art after consideration of the present disclosure that the first volume 128 would typically be completely or almost completely filled with the elements 212 of the displacement insert 126. The examples presented in FIGS. 2B-2D are, like the example presented in FIG. 2A, examples of an "in-line" configuration of a parcelizer device 122 formed from a container 120 and the displacement structure 124. In particular, the containers 120 in such examples include an inlet 116 at a first end of the container 120 and outlet 132 at a second end of the container 120.

Accordingly, different configurations of containers 120 and/or displacement structures 124 can be provided in implementing embodiments of the present disclosure. In at least some of the embodiments, the parcelizer device 122 presents pathways with cross-sections of from about 3 mm to about 4 mm to fat parcels being drawn therethrough. In accordance with other embodiments, the pathways presented by the parcelizer device 122 have a maximum cross section of 3 mm or less. Moreover, a non-linear pathway, with tight turns and turns that reverse direction as compared to preceding or subsequent turns, are provided. This configuration is believed to provide fat parcels within a favorable size range, while avoiding clogging. An example of a desired fat parcel size range that can be obtained using embodiments of the present disclosure is 1-3 mm. Displacement inserts 126 can be formed from various materials. For example, elements 212 or 216 can comprise silicon or polymer beads that are 2-6 mm in diameter and that have 1-3 mm through-holes. As further examples, elements 220 can comprise styrene tubes or straws that are about 1 cm in length and that have 1-3 mm through-holes.

Figure 3:
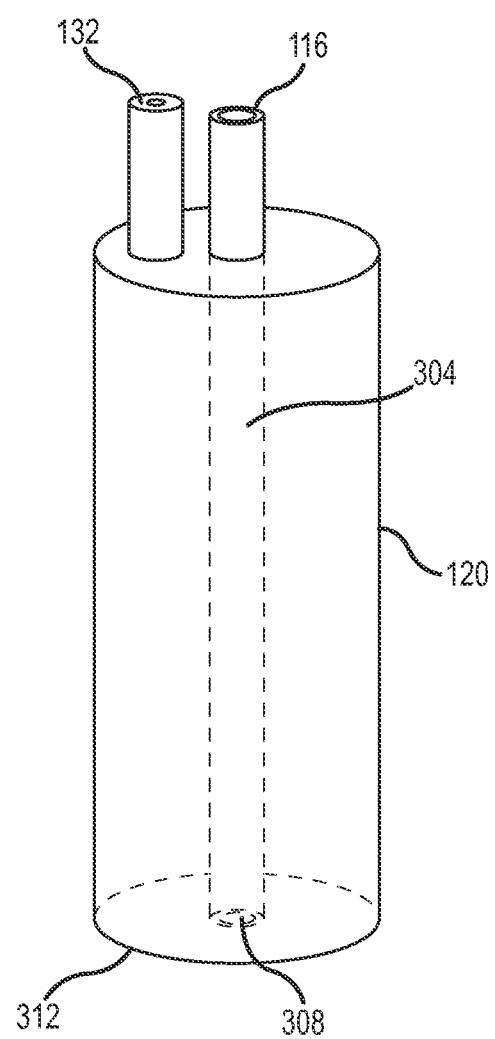
FIG. 3 depicts a container in accordance with other embodiments of the present disclosure.

FIG. 3 illustrates a container 120 in accordance with further embodiments of the present disclosure. In this embodiment, the inlet 116 is associated with an internal conduit 304 having an opening 308 adjacent a closed end 312 of the container 120, opposite the end of the container 120 at which the length of tubing 108 connects to the inlet 116. The outlet 132 is at the same end as and next to the connection between the inlet 116 portion of the length of tubing 108 (see, e.g., FIG. 1A). As can be appreciated by one of skill the art after consideration of the present disclosure, a container 120 as illustrated in FIG. 3 can be associated with various displacement inserts 126, including but not limited to displacement inserts 126 comprising a plurality of elements 212, 216, 220 that can be poured into and loosely held by the container 120.

Although an example system 100 is shown (see, e.g., FIG. 1A) in which the parcelizer device 122 includes a displacement structure 124 that is positioned between the cannula 108 and a reservoir 116, other configurations are possible. For example, the container 120 can be integral to a cannula handle. In such an embodiment, the first volume 128 containing the displacement unit 126 is provided by the cannula handle or an associated structure. In accordance with still other embodiments, the first volume 128 can be provided by the cannula 104 itself, for example in a portion of the rigid tubing forming the cannula 104.

Figure 4:
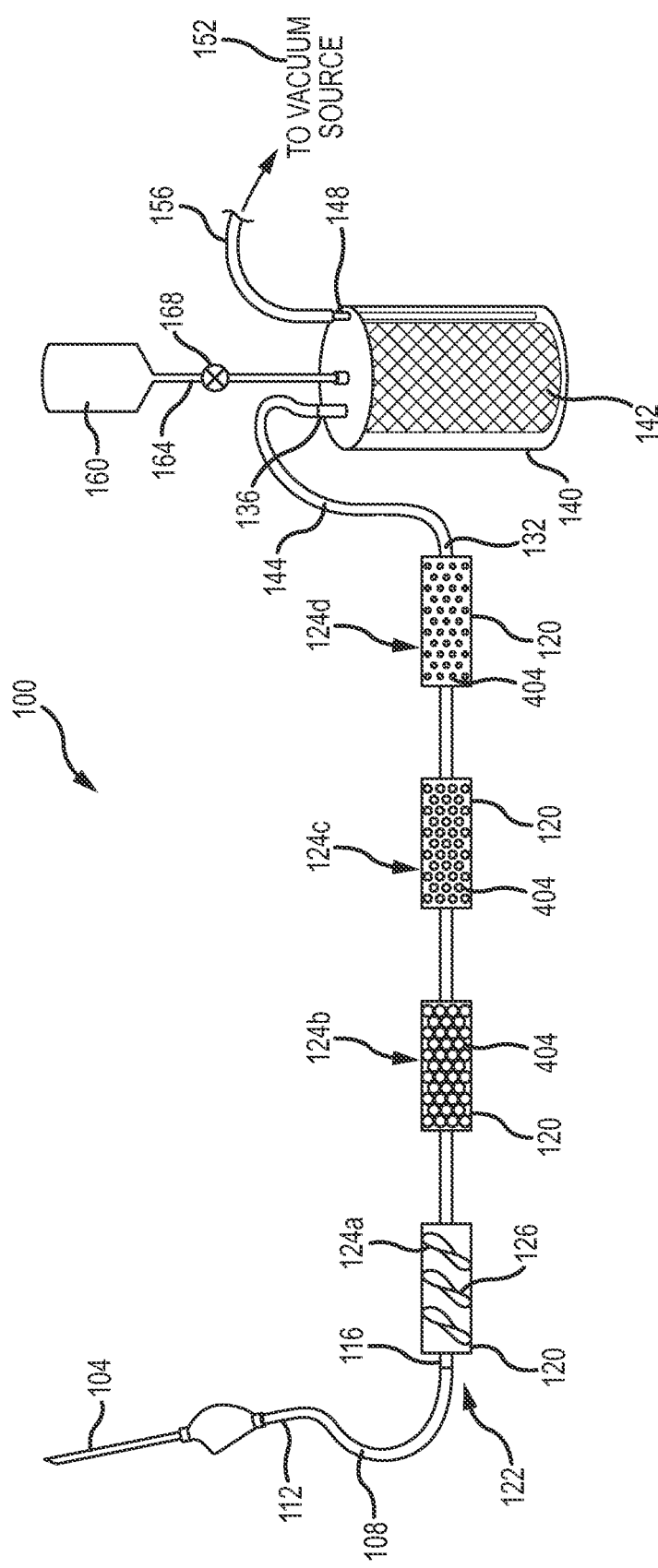
FIG. 4 depicts components of a tissue parcelization system in accordance with embodiments of the present disclosure.

FIG. 4 depicts a tissue parcelization system 100 in accordance with other embodiments of the present disclosure. In general, the system 100 includes a cannula 104, and a length of tubing 108 connecting an outlet 112 of the cannula 104 to the inlet 116 of a container 120. As an example, but without limitation, the cannula 104 can have a 3 mm outside diameter, with 4 oval holes that are about 2 mm by 6 mm. Other examples of cannula 104 dimensions include those with a 3 mm outside diameter and 12 round 2 mm holes; a 4 mm outside diameter with 4 oval holes that are about 2 mm by 6 mm; and a 4 mm outside diameter with 12 round holes that are 2 mm in diameter. Other cannula configurations are also suitable. Such cannulas given as examples in connection with this example tissue parcelization system 100 can also be used in connection with other systems 100 in accordance with embodiments of the present disclosure.

The system 100 also includes a parcelizer device 122 that is formed from a series of displacement structures 124a-d. The displacement structures 124a-d may be connected to one another directly, or by short lengths of tubing. In accordance with still other embodiments, multiple displacement structures 124 can be disposed within the same container 120 or within different chambers within the same container 120. In the example of FIG. 4, a first displacement structure 124a incorporates an auger type displacement insert or element 126, with passages that provide 4 mm of clearance. In the auger type displacement structure 124, the spaces between adjacent blades of the auger can be about 4 mm. In addition, about 4 mm or clearance can be provided between the outer edges of the blades and the inner surface of the container 120. A second displacement structure 124b in this embodiment incorporates spheres or balls 404 as a displacement insert 126 that, compared to balls 404 in subsequent displacement structures 124c and 124d described below, are relatively large. For instance, the diameter of the balls can be selected such that the maximum spacing between adjacent balls 404 is about 3 mm. A third displacement structure 124c incorporates balls 404 that, compared to balls 404 in the second 124b and fourth 124d displacement structures, are medium sized. For example, the diameter of the balls can be selected such that the maximum spacing between adjacent balls 404 can be about 2 mm. The fourth displacement structure 124d incorporates balls 404 that are smaller than the previous displacement structures 124b and 124c. For example, the maximum spacing between adjacent balls can be about 1 mm. As can be appreciated by one of skill in the art from the present disclosure, the auger of the first displacement structure 124a defines a convoluted, circuitous, or otherwise non-linear path through which tissue drawn in through the inlet 116 of the container and out an outlet 132 of the container 120 must pass. Similarly, the balls 404 packed within the containers 120 of the second 124b, third 124c, and fourth 124d displacement structures define non-linear paths through which the tissue must traverse while passing from the inlet to the outlet.

The outlet 132 of the container 120 of the last displacement structure 124d in the series can be connected to an inlet 136 of a reservoir 140 by a reservoir conduit 144. The reservoir 140 can contain a filter element 142. An outlet 148 of the reservoir 140 can then be connected to a vacuum source 152 by a length of vacuum conduit 156. In addition, the system 100 can include a wash fluid reservoir 160 connected to the reservoir 140 by a wash fluid conduit 164. An adjustable valve 168, such as a one-way valve for example, can be included to control the flow of the wash fluid into the reservoir 140.

FIG. 5 depicts portions of a system 100 in accordance with other embodiments of the present disclosure. In this example, three displacement structures 124a-c are provided as part of the parcelizer device 122. Moreover, these displacement structures 124 all incorporate auger type displacement elements or inserts 126. As shown, the transverse diameter of the displacement elements or inserts 126 progressively decrease from the first displacement structure 124a through the third displacement structure 124c. Accordingly, the non-linear pathways through the displacement structures 124 are progressively smaller. In accordance with still other embodiments, the pathway or pathways within a single displacement structure 124 can become progressively smaller.

FIGS. 6A and 6B depict portions of a system 100 with a parcelizer device 122 that incorporates a displacement structure 124 that includes a container 120 and a plurality of filter elements 126a-d. Each filter element 126 may comprise a mesh, screen, grater, perforated plate, mat, paper or other filter material or element that extends across the volume defined by the container 120. As best shown in FIG. 7A, the filter elements 126 are arranged in series. Moreover, the pathways defined by each of the filter elements 126 may become progressively smaller from the inlet 116 to the outlet 132 of the displacement structure 124. The change in the pore or aperture size of the different filter elements 126 is shown in FIG. 6B.

FIGS. 7A and 7B depict a portion of a parcelizer device 122 with a displacement structure 124 that includes a first insert 126a comprising a plurality of relatively large spheres or balls 404 in a first portion of a container 120, and a second insert 126b comprising a plurality of relatively small spheres or balls 404 in a second portion of the container 120. A screen or other tissue permeable barrier can be provided to define the portions or chambers of the container 120. The large balls 404 can be near the inlet 116 to define a first or maximum path size, and the small balls 404 can be near the outlet 132 to define a second or minimum path size.

Figure 8:
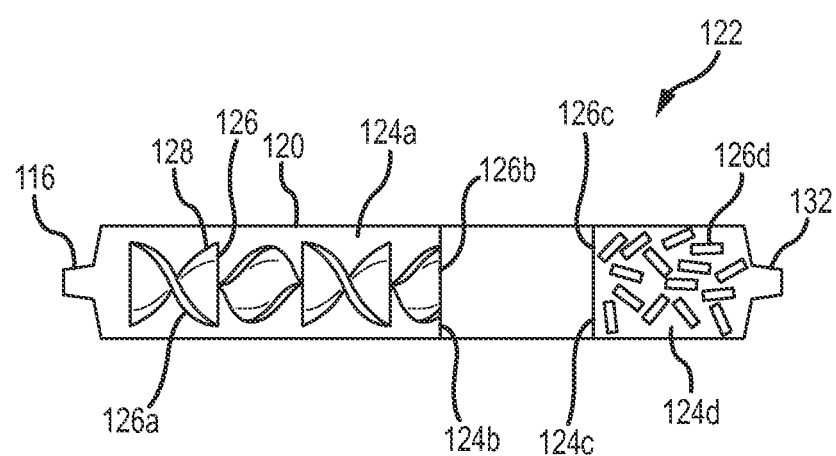
FIG. 8 depicts displacement structures in accordance with other embodiments of the present disclosure.

FIG. 8 depicts a parcelizer device 122 having a single container 120 and a variety of displacement inserts or filter elements 126 forming displacement structures 124. In particular, in this example, near an inlet 116 a first displacement structure 124a includes a first insert 126a in the form of an auger. Moreover, the first insert 126a has a maximum diameter that is less than an interior diameter of the container 120, thereby defining an annular pathway 128. As can be appreciated by one of skill in the art after consideration of the present disclosure, the first insert 126a can be maintained in position through radial arms that extend at intervals from the first insert 126a to an interior wall of the container 120, or through other support structures. The parcelizer device 122 also includes a second insert 126b forming a second displacement structure 124b. In this example, the second displacement element or insert 126b can be in the form of a perforated plate or screen having holes of a selected size. As fat parcels are pushed further along the parcelizer device 122, a third displacement structure 124c that includes a third insert or element 126c is encountered. In this example, the third insert 126c is a perforated plate with a selected hole size that is smaller than the selected hole size of the second insert or element 126b. Next, a fourth displacement structure 126d, in this example a plurality of tubes or cylinders, is encountered. These tubes or cylinders 126d, which are confined within a volume between the third insert 126c and the outlet 132 of the container 120, present multiple circuitous paths to the tissue, further reducing the size of fat parcels within the tissue as the tissue is passed from the inlet 116 to the outlet 132.

Figure 9:
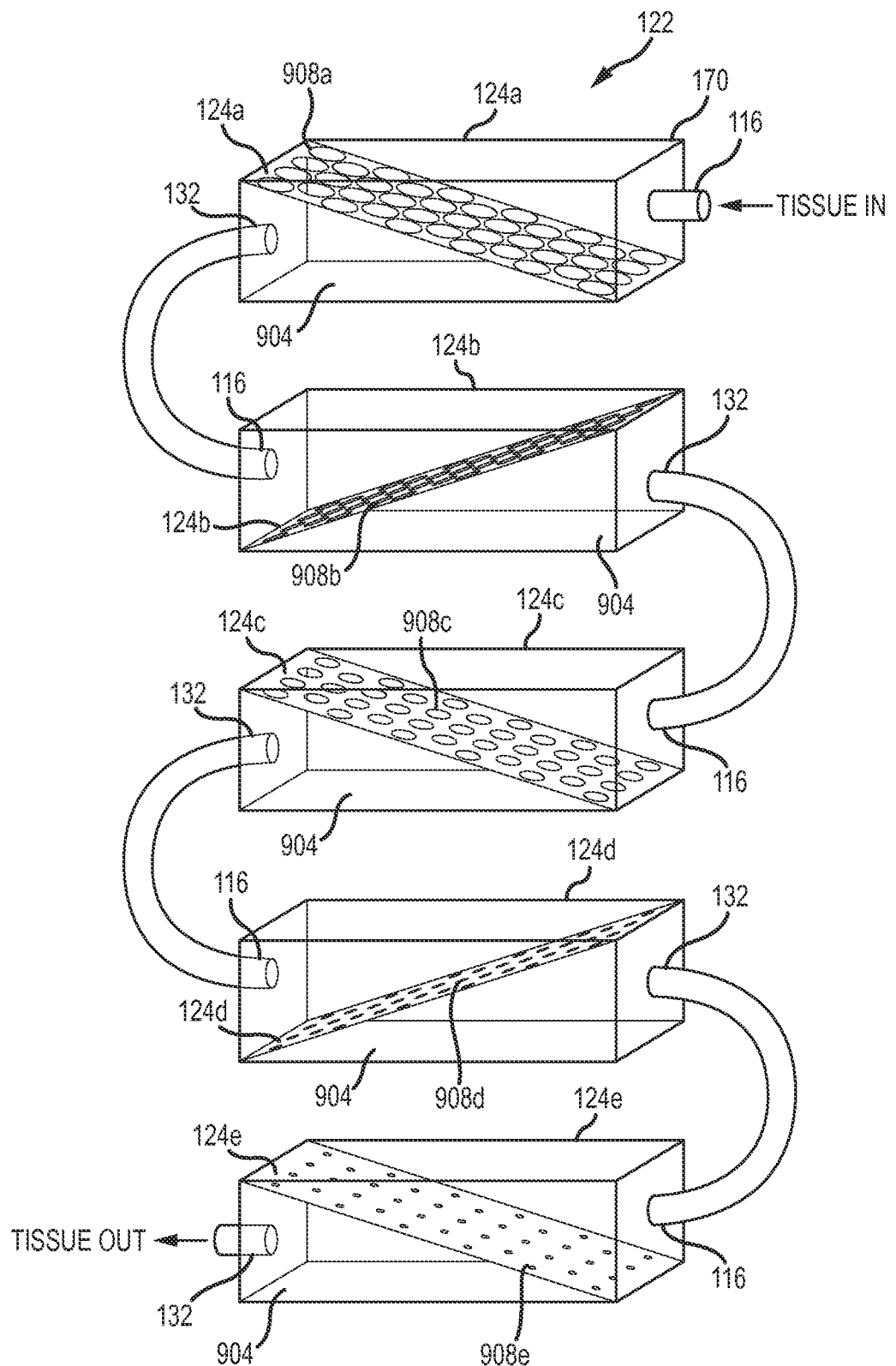
FIG. 9 depicts displacement structures in accordance with other embodiments of the present disclosure.

FIG. 9 depicts a parcelizer device 122 in accordance with still other embodiments of the present disclosure. More particularly, the parcelizer device 122 includes a plurality of displacement structures 124a-e. Each of the displacement structures 124 includes a container 120 and a perforated plate as a filter element or insert 126. For ease of illustration, at least the side wall 904 of each container 120 closest to the viewer is depicted as being formed from a transparent material. Indeed the entire container 120 can be transparent. Alternatively some or all of the container 120 walls can be translucent or opaque. The filter element 126 is arranged within the container 120 relative to the inlet 116 and the outlet 132 of each displacement structure such that a sheer motion or effect is introduced as tissue moves from the inlet, across and through the filter element 126, and out the outlet 132 of each container 120. In addition, as shown in the figure, the filter elements 126 can be disposed at an angle within the associated container 120 to promote movement of tissue, and in particular fat parcels, through the perforations or holes 908 of the filter element 126. Accordingly, the filter elements 126 can produce a "grating" effect. To enhance this effect, each of the perforations 908 can be associated with a raised portion around some or all of the perforation 908. Accordingly, the perforations 908 can be configured with cutting edges like a common cheese grater. For instance a round or square hole 908 surrounded by raised cutting edges can be used.

The displacement structures 124*a-e* may include perforations 908 of different sizes. In general, the holes can range in size from 0.1 mm to 2 cm. As examples, the filter element 126*a* of the displacement structure 124*a* nearest the inlet 116 to the parcelizer device 122 can have perforations or holes 908*a* that are 10 mm in diameter. The second displacement structure 124*b* can include a filter element 126*b* with perforations or holes 908*b* that are 7 mm in diameter. The third displacement structure 124*c* can include a filter element 126*c* with perforations or holes 908*c* that are 4 mm in diameter. The fourth displacement structure 124*d* can include a filter element 126*d* with perforations or holes 908*d* that are 2 mm in diameter. The fifth displacement structure 124*e* can include a filter element 126*e* with perforations or holes 908*e* that are 1 mm in diameter. The holes can be round, oval, square, rectangular, triangular, "U" shaped, or any other shape. The filter elements 126 can be formed from a polymer, stainless steel, glass, aluminum, or a rigid mesh.

In the example parcelizer device 122 of FIG. 9, each of the displacement structures 124 is connected to one or more adjacent displacement structures by lengths of transfer tubing 912. Moreover, each displacement structure 124 includes an inlet 116 and an outlet 132. In accordance with other embodiments, more than one filter element 126 can be included within a displacement structure 124. In addition, as with other embodiments, a parcelizer device 122 incorporating one or more filter elements 116 that includes balls or perforations can also include other types of displacement structures 124, such as but not limited to mesh screens, augers, beads, straws, in any combination. Moreover, the containers 120 need not be rectangular boxes, but can be any desired shape. In addition, the size of the holes given in the forgoing examples are exemplary only, and other sizes can end progressions of sizes between displacement structures within a series of displacement structures 124 can be used.

In various exemplary embodiments illustrated and described herein, particular combinations of displacement structures 124 and sequences of displacement structures 124 are provided. However, other combinations or arrangements are possible. For example, a parcelizer device 122 can include any number of displacement structures 124 having any type and/or size of displacement inserts 126 or holes. As can be appreciated by one of skill in the art after consideration of the present disclosure, a parcelizer device 122 featuring a plurality of displacement structures 124 typically provides maximum path sizes that gradually decrease from the inlet towards the outlet. Such a configuration can provide tissue of a reduced maximum packet size, while avoiding clogging of the displacement structures 124.

Accordingly, various embodiments of parcelizer devices 122 have been described with some particularity. As can be appreciated by one of skill in the art after consideration of the present disclosure, the various parcelizer devices 122 can be used in association with a power source comprising a vacuum source 152 that pulls tissue containing fat parcels through the parcelizer device 122. Examples of vacuum sources 152 include, but are not limited to, manual syringes, power syringes, bulbs, aspirators, reverse peristaltic pumps, and/or gravity. Parcelizer devices 122 as disclosed herein can also be used in connection with a power source in the form of a pressure source or pump 160 that pushes tissue containing fat parcels through the parcelizer device 122. Examples of power sources 160 therefore include, but are not limited to, a syringe, a syringe gun, a reinjection gun, a canister of compressed air, a compressor, and a peristaltic pump. After tissue has been passed through a parcelizer device 122, that tissue can be reinjected into a body, either directly, or after further processing. In addition, tissue can be passed through a parcelizer device 122 immediately after that tissue is withdrawn from a body, or after that tissue has been processed.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications required by the particular application or use of the invention. It is intended that the appended claims be construed to include alternative embodiments to the extent permitted by the prior art.

What is claimed is:

1. A system for sizing fat parcels, comprising:
   a cannula;
   a container, wherein the container defines a first volume, wherein the container has an inlet connected to an outlet of the cannula, and wherein the container includes an outlet;
   a displacement structure comprising:
     a first filter element having a plurality of perforations, wherein the first filter element is transverse to a length of the container;
     a second filter element having a plurality of perforations, wherein the second filter element is transverse to the length of the container, wherein the first and second filter elements are spaced apart from one another, and wherein the first and second filter elements define second, third, and fourth volumes within the first volume of the container;
     a first insert in the second volume; and
     a second insert in the third volume, wherein the first and second inserts define at least a first non-linear path between the inlet and the outlet of the container, and wherein the first and second inserts are different from one another; and
   a tissue reservoir, wherein the tissue reservoir includes an inlet that is interconnected to the outlet of the container.

2. The system of claim 1, wherein the first insert of the displacement structure comprises a plurality of beads having at least a first through hole, and wherein the plurality of beads are spherical.

3. The system of claim 1, wherein the first insert of the displacement structure comprises a plurality of beads having at least a first through hole, and wherein the plurality of beads are faceted.

4. The system of claim 1, wherein the container is a length of tubing.

5. The system of claim 4, wherein the inlet of the container is at a first end of the length of tubing, and wherein the outlet of the container is at a second end of the length of tubing.

6. The system of claim 1, further comprising:
a vacuum pump interconnected to the outlet of the container.

7. The system of claim 1, further comprising:
a plurality of displacement structures located in different containers.

8. The system of claim 1, wherein the first insert comprises a plurality of cylinders.

9. A method of sizing fat parcels, comprising:
moving tissue containing fat parcels into a container; and
passing the tissue through the interior volume of the container, including:
passing the tissue past an auger that is located within the interior volume of the container and that is fixed relative to the container, passing the tissue through a first filter element located within the interior volume of the container, passing the tissue through a second filter element located within the interior volume of the container, and passing the tissue through a plurality of elements located within the interior volume of the container and confined between the second filter element and an outlet of the container, wherein the plurality of elements includes beads or cylinders.

10. A system for sizing fat parcels, comprising:
a cannula;
a container wherein the container defines a first volume, wherein the container has an inlet connected to an outlet of the cannula, and wherein the container includes an outlet;
a displacement structure comprising:
a first filter element having a plurality of perforations, wherein the first filter element is transverse to a length of the container;
a second filter element having a plurality of perforations, wherein the second filter element is transverse to the length of the container, wherein the first and second filter elements are spaced apart from one another and wherein the first and second filter elements define second, third, and fourth volumes within the first volume of the container;
a first insert in the second volume; and
a second insert in the third volume, wherein the first and second inserts define at least a first non-linear path between the inlet and the outlet of the container; and
a tissue reservoir, wherein the tissue reservoir includes an inlet that is interconnected to the outlet of the container, wherein the first insert comprises an element that defines at least a first pathway that revolves in a first direction with respect to a first axis of the container for a first segment along the first axis, wherein the at least first pathway revolves in a second direction with respect to the first axis of the container for a second segment along the first axis, and wherein the second insert comprises a plurality of beads.

11. The system of claim 10, wherein the first insert of the displacement structure is fixed relative to the container and further comprises a central shaft aligned with a first axis of the container and at least a first helical surface surrounding the central shaft.

12. The system of claim 10, wherein the plurality of beads are spherical.

13. A system for sizing fat parcels, comprising:
a cannula;
a container, wherein the container defines a first volume, wherein the container has an inlet connected to an outlet of the cannula, and wherein the container includes an outlet;
a displacement structure comprising:
first filter element having a plurality of perforations, wherein the first filter element is transverse to a length of the container;
a second filter element having a plurality of perforations wherein the second filter element is transverse to the length of the container, wherein the first and second filter elements are spaced apart from one another, and wherein the first and second filter elements define second, third, and fourth volumes within the first volume of the container;
a first insert in the second volume; and
a second insert in the third volume, wherein the first and second inserts define at least a first non-linear lath between the inlet and the outlet of the container; and
a tissue reservoir, wherein the tissue reservoir includes an inlet that is interconnected to the outlet of the container, wherein the first insert of the displacement structure comprises a plurality of beads having a first diameter, wherein the second insert of the displacement structure comprises a plurality of beads having a second diameter, and wherein the first diameter is different than the second diameter.

14. The system of claim 13, wherein the plurality of beads are spherical.

15. A system for sizing fat parcels, comprising:
a cannula;
a container, wherein the container defines a first volume, wherein the container has an inlet connected to an outlet of the cannula, and wherein the container includes an outlet;
a displacement structure comprising:
a first filter element having a plurality of perforations, wherein the first filter element is transverse to a length of the container;
a second filter element having a plurality of perforations, wherein the second filter element is transverse to the length of the container, wherein the first and second filter elements are spaced apart from one another, and wherein the first and second filter elements define second, third, and fourth volumes within the first volume of the container;
a first insert in the second volume; and
a second insert in the third volume, wherein the first and second inserts define at least a first non-linear path between the inlet and the outlet of the container; and
a tissue reservoir, wherein the tissue reservoir includes an inlet that is interconnected to the outlet of the container, wherein the first insert comprises an auger, and wherein the second insert comprises a plurality of cylinders.

16. The system of claim 15, wherein the second volume is between the inlet to the container and the first filter element, wherein the third volume is between the second filter element and the outlet of the container, and wherein the fourth volume is between the first and second filter elements.

* * * * *